United States Patent
Suzuki et al.

(10) Patent No.: US 6,239,305 B1
(45) Date of Patent: *May 29, 2001

(54) METHOD FOR PRODUCING OPTICALLY ACTIVE PHENYLPROPIONIC ACID DERIVATIVE

(75) Inventors: Takayuki Suzuki; Takayuki Hamada; Kunisuki Izawa, all of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/455,936

(22) Filed: Dec. 7, 1999

Related U.S. Application Data

(63) Continuation of application No. 09/249,848, filed on Feb. 16, 1999, now Pat. No. 6,031,121.

(30) Foreign Application Priority Data

Feb. 16, 1998 (JP) .................................................. 10-32791

(51) Int. Cl.[7] .................................................. C07C 327/20
(52) U.S. Cl. .................................................. 558/254; 558/256
(58) Field of Search .................................................. 558/254

(56) References Cited

U.S. PATENT DOCUMENTS

| | | | |
|---|---|---|---|
| 4,722,810 | 2/1988 | Delaney et al. | 260/402 |
| 4,798,904 | 1/1989 | Delaney et al. | 558/254 |
| 5,136,076 | 8/1992 | Duhamel et al. | 558/254 |
| 5,208,255 | 5/1993 | Duhamel et al. | 514/513 |
| 5,210,266 | 5/1993 | Mimura et al. | 558/254 |
| 5,296,509 | 3/1994 | Duhamel et al. | 514/513 |
| 5,331,008 | 7/1994 | Duhamel et al. | 514/513 |
| 5,646,313 | 7/1997 | Danvy et al. | 549/441 |
| 6,031,121 | * 2/2000 | Suzuki et al. | 558/254 |

OTHER PUBLICATIONS

B.R. Neustadt et al, "Mercaptoacyl Amino Acid Inhibitors of Atriopeptidase. 1. Structure–Activity Relationship Studies of Methionine and S–Alkylcysteine Derivatives", Journal of Medicinal Chemistry, vol. 37, No. 15, pp. 2461–2476, Jul. 22, 1994.

P. Deprez et al., "Thiol Inhibitors of Endothelin–Converting Enzyme", Bioorganic & Medicinal Chemistry Letters, vol. 6, No. 19, pp. 2317–2322, Oct. 8, 1996.

M. Nakano et al., "Synthesis of Renin Inhibitors Containing a Sulfonemethylene Isostere at Their N–Terminals", Chemistry Letters, No. 4, pp. 505–508, Apr. 1990.

* cited by examiner

Primary Examiner—Paul J. Killos
(74) Attorney, Agent, or Firm—Oblon, Spivak, McClelland, Maier & Neustadt, P.C.

(57) ABSTRACT

Optically active N-(S-2-acetylthiomethyl-1-oxo-3-phenylpropyl)-glycine benzyl ester useful as an enkephalin inhibitory agent or ACE inhibitory agent can be produced at low cost in an industrial manner, by a method comprising subjecting optically active 2-hydroxymethyl-3-phenylpropionic acid and glycine benzyl ester to condensation to subsequently convert the hydroxyl group into an elimination group, and substituting the elimination group with an acetylthio group.

6 Claims, No Drawings

METHOD FOR PRODUCING OPTICALLY ACTIVE PHENYLPROPIONIC ACID DERIVATIVE

This application is a continuation of U.S. application Ser. No. 09/249,848 filed Feb. 16, 1999, now U.S. Pat. No. 6,031,121.

BACKGROUND OF THE INVENTION

1. Field of the Invention

The present invention relates to a method for producing optically active N-(2-acetylthiomethyl-1-oxo-3-phenylpropyl)-amino acid ester. The present invention is useful for producing optically active N-(2-acetylthiomethyl-1-oxo-3-phenylpropyl)-glycine benzyl ester.

2. Description of the Related Art (S)-N-(2-acetylthiomethyl-1-oxo-3-phenylpropyl)-glycine benzyl ester with an inhibitory action against angiotensin converting enzyme is useful as therapeutic agents of deteriorated cardiovascular system, hypertension, cardiac function impairment and liver function impairment. Alternatively, the (R) form thereof with an inhibitory action of enkepharinase is useful as analgesic, antidiarrheic, and antacid (JP-A-2-161 and JP-A-8-59606). Methods for producing optically active N-(2-acetylthiomethyl-1-oxo-3-phenylpropyl)-glycine benzyl ester having been known so far include a method comprising optically resolving racemic 2-acetylthiomethyl-3-phenylpropionic acid by using ephedrine and subjecting one of the resulting products to condensation with glycine benzyl ester and N,N'-dicyclohexylcarbodiimide (JP-A-8-59606). According to the method, however, the efficiency of the optical resolution of 2-acetylthiomethyl-3-phenylpropionic acid with ephedrine is so low that the method is not practical. Furthermore, the method generates such an enormous volume of sulfur-containing wastes that the method cannot be said to be an industrially advantageous method.

SUMMARY OF THE INVENTION

It is an object of the present invention to provide a method for producing optically active N-(2-acetylthiomethyl-1-oxo-3-phenylpropyl)-amino acid ester, particularly optically active N-(2-acetylthiomethyl-1-oxo-3-phenylpropyl)-glycine benzyl ester, in an inexpensive manner suitable for industrial production.

The present inventors have made investigations so as to overcome the problems. Consequently, the inventors have found a method for producing N-(2-acetylthiomethyl-1-oxo-3-phenylpropyl)-amino acid ester, the method comprising subjecting optically active 2-hydroxymethyl-3-phenylpropionic acid and an amino acid ester to condensation to subsequently convert the hydroxyl group into an elimination group, and substituting the elimination group with an acetylthio group. Thus, the invention has been achieved.

More specifically, the invention relates to a method for producing an optically active N-(2-acetylthiomethyl-1-oxo-3-phenylpropyl)-amino acid ester, represented by the general formula (IV):

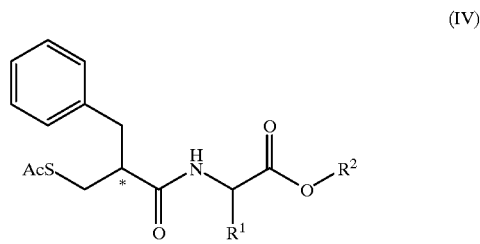

wherein $R_1$ represents hydrogen, an amino acid side chain or a protected amino acid side chain; $R_2$ represents a linear or branched $C_1$ to $C_{18}$ alkyl group, or a benzyl group which may or may not have a substituent; AcS represents an acetylthio group; and * represents an optically active carbon atom, the method comprising subjecting optically active 2-hydroxymethyl-3-phenylpropionic acid, represented by the general formula (I):

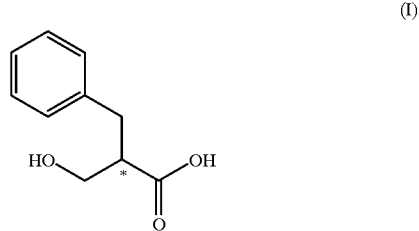

wherein * represents an optically active carbon atom, to reaction with an amino acid ester or a salt thereof for conversion into optically active N-(2-hydroxymethyl-1-oxo-3-phenylpropyl)-amino acid ester, represented by the general formula (II):

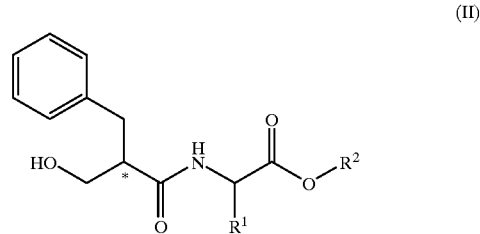

wherein $R_1$ and $R_2$ independently represent the same as described above and * represents an optically active carbon atom; activating the hydroxyl group of the hydroxymethyl group at the 2-position for conversion into optically active N-acylamino acid ester, represented by the general formula (III):

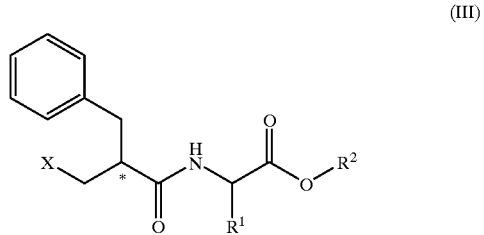

wherein $R_1$ and $R_2$ independently represent the same as described above; X represents chlorine, bromine, iodine, a linear, branched or cyclic $C_1$–$C_6$ alkylsulfonyloxy group which may or may not have a substituent, or a $C_6$–$C_{18}$ arylsulfonyloxy group; and * represents an optically active carbon atom; and further subjecting the resulting optically active N-acylamino acid ester to reaction with a thioacetate salt or thioacetic acid in the presence of a base.

The present invention is particularly useful for producing optically active N-(2-acetylthiomethyl-1-oxo-3-phenylpropyl)-glycine benzyl ester. More specifically, the invention relates to a method for producing optically active N-(2-acetylthiomethyl-1-oxo-3-phenylpropyl)-glycine benzyl ester, represented by the general formula (IV):

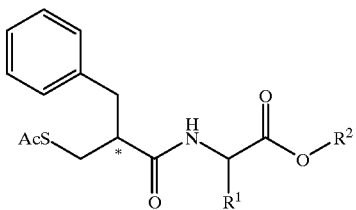

(IV)

wherein $R_1$ represents hydrogen; $R_2$ represents a benzyl group; AcS represents an acetylthio group; and * represents an optically active carbon atom, the method comprising subjecting optically active 2-hydroxymethyl-3-phenylpropionic acid, represented by the general formula (I):

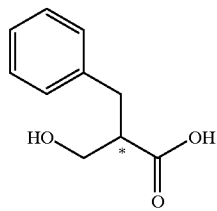

(I)

wherein * represents an optically active carbon atom, to reaction with glycine benzyl ester or a salt thereof for conversion into optically active N-(2-hydroxymethyl-1-oxo-3-phenylpropyl)-glycine benzyl ester, represented by the general formula (II):

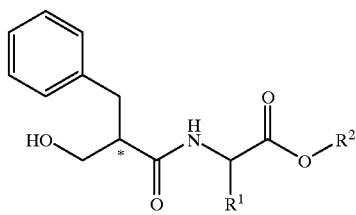

(II)

wherein $R_1$ represents hydrogen; $R_2$ represents benzyl group; and * represents an optically active carbon atom; activating the hydroxymethyl group at the 2-position for conversion into optically active N-acylglycine benzyl ester, represented by the general formula (III):

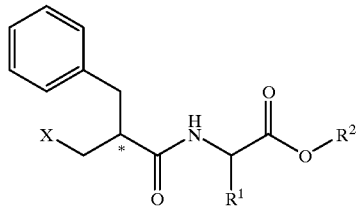

(III)

wherein X represents chlorine, bromine, iodine, a linear, branched or cyclic $C_1$–$C_6$ alkylsulfonyloxy group which may or may not have a substituent, or a $C_6$–$C_{18}$ arylsulfonyloxy group; $R_1$ represents hydrogen; $R_2$ represents a benzyl group; and * represents an optically active carbon atom; and further subjecting the resulting N-acylglycine benzyl ester to reaction with a thioacetate salt or thioacetic acid in the presence of a base.

According to the invention, the optically active carbon atom can be in the S configuration or in the R configuration.

Additionally, significant intermediates according to the method, namely the optically active N-(2-hydroxymethyl-1-oxo-3-phenylpropyl)-glycine benzyl ester represented by the general formula (II) and the optically active N-acylglycine benzyl ester represented by the general formula (III) are also encompassed within the scope of the present invention.

DETAILED DESCRIPTION OF THE INVENTION

The optically active 2-hydroxymethyl-3-phenylpropionic acid (1) for use as a raw material in accordance with the invention, can be prepared by optically resolving racemic 2-hydroxymethyl-3-phenylpropionic acid by using an optically active amine such as (1R,2S)-(+)-cis-1-amino-2-indanol (JP97-270680).

The amino acid in the amino acid ester or a salt thereof for use as the raw material in accordance with the invention includes glycine, phenylglycine, alanine, glutamine, asparagine, valine, leucine, isoleucine, proline, methionine, serine, threonine, phenylalanine, naphtylalanine, tyrosine, 3,4-dihydroxyphenylalanine, tryptophan, histidine, glutamic acid, aspartic acid, lysine, and arginine. These amino acids may satisfactorily have substituents at the side chains thereof. Examples of substituents include $C_1$–$C_6$ alkyl groups, $C_1$–$C_6$ alkoxy groups, a halogen group and a nitro group. Furthermore, any reactive functional group within the side chains is preferably protected with protective groups for use in peptide synthesis, for example ester-type protective groups such as methyl ester, ethyl ester, and benzyl ester for carboxyl group; acyl groups such as formyl group, acetyl group, trifluoroacetyl group, benzoyl group, t-butyloxycarbonyl group and benzyloxycarbonyl group for amino group; and ether-type protective groups such as benzyl ether and t-butyl ether and ester-type protective groups such as acetyl or benzoyl for hydroxyl group.

In the amino acid ester, a-carboxyl group has been esterified preliminarily. The ester includes for example methyl ester, ethyl ester and benzyl ester. The ester may optionally have substituents. Examples of substituents include $C_1$–$C_6$ alkyl groups, $C_1$–$C_6$ alkoxy groups, a halogen group and a nitro group. Because the α-carboxyl group of the amino acid in the final compound, namely N-(2-acetylthiomethyl-1-oxo-3-phenylpropyl)-glycine benzyl ester as one of the objective compounds of the invention, is prepared in the form of benzyl ester, the amino acid ester is preferably in the form of benzyl ester. The amino acid ester in the objective compounds may satisfactorily be deprotected in a conventional manner.

The reaction of optically active 2-hydroxymethyl-3-phenylpropionic acid (1) with an amino acid ester to convert the phenylpropionic acid (I) into optically active N-(2-hydroxymethyl-1-oxo-3-phenylpropyl)-amino acid ester (II) is promoted by a condensation process for use in general peptide synthesis.

More specifically, optically active 2-hydroxymethyl-3-phenylpropionic acid (I) is subjected to reaction with an amino acid ester in the presence of a condensation agent in a solvent.

The condensation agent for use in the reaction includes N,N'-dicyclohexylcarbodiimide, a water-soluble carbodiimide, carbonyldiimidazole, and diphenylphosphoryl azide. Glycine benzyl ester may be used in the free form or in the form of a salt with hydrochloric acid, sulfuric acid, p-toluenesulfonic acid, methanesulfonic acid and the like. Use may be made of solvents such as hydrocarbon halides such as dichloromethane and chloroform; ethers such as tetrahydrofuran and methyl tert-butyl ether; acetate esters such as ethyl acetate and isopropyl acetate; nitriles such as acetonitrile; aromatic hydrocarbons such as toluene and xylene; dimethylformamide and dimethylsulfoxide.

Additionally, bases such as triethylamine, pyridine, N-methylmorpholine, and 4-dimethylaminopyridine may optionally be present concurrently in the reaction system. Still further, additives such as N-hydroxysuccinimide and 1-hydroxybenzotriazole may also be used.

The conversion of optically active N-(2-hydroxymethyl-1-oxo-3-phenylpropyl)-amino acid ester (II) into optically active N-acylamino acid ester (III) by activating the hydroxyl group of the hydroxymethyl group at 2-position of the amino acid ester (II) can be promoted by alkylsulfonation, arylsulfonation or halogenation or the like for general use in the activation of the hydroxyl group.

The hydroxyl group is alkylsulfonated or arylsulfonated by the action of an sulfonation agent in the presence of an activation base. The sulfonation agent includes methanesulfonyl chloride, p-toluenesulfonyl chloride, benzenesulfonyl chloride, p-nitrobenzenesulfonyl chloride, and trifluoromethanesulfonyl chloride. The activation base includes triethylamine, pyridine, 4-dimethylaminopyridine, and N-methylmorpholine.

The hydroxyl group is halogenated via the action of halogenating agents such as thionyl chloride, phosphorus trichloride, phosphorus pentachloride, phosphorus oxychloride, and phosphorus tribromide or via the action of halogenating agents, in the presence of triphenylphosphine, such as N-chlorosuccinimide, N-bromosuccinimide, bromide, carbon tetrachloride and carbon tetrabromide. Alternatively, the halogenation of the hydroxyl group comprises alkylsulfonating, arylsulfonating or haloformylating the hydroxyl group, and subsequently subjecting the resulting halogenated hydroxyl group to reaction with lithium chloride, lithium bromide, sodium bromide, potassium bromide, magnesium bromide, tetra-(n-butyl) ammonium bromide or sodium iodide.

The optically active 2-hydroxymethyl-3-phenylpropionic acid (1) can be converted into-optically active N-acylamino acid ester (III) at one step, by subjecting the 2-hydroxymethyl-3-phenylpropionic acid (I) to reaction with thionyl chloride or thionyl bromide or the like to convert the carboxyl group into an acid chloride and concurrently preparing the hydroxyl group into an elimination group such as halogen or sulfinyloxychloride group and subjecting the elimination group to reaction with amino acid ester.

The optically active N-acyl-amino acid ester (III) can be converted into optically active N-(2-acetylthiomethyl-1-oxo-3-phenylpropyl)-amino acid ester (IV), by subjecting the optically active N-acylamino acid ester (III) to reaction with a thioacetate salt or reaction with thioacetic acid in the presence of a base. The thioacetate salt includes potassium thioacetate, sodium thioacetate, lithium thioacetate, and cesium thioacetate.

For the aforementioned reaction, any inorganic base or organic base may be used in the co-existence of thioacetic acid; the inorganic base includes sodium hydroxide, potassium hydroxide, sodium carbonate, potassium carbonate, and cesium carbonate; and the organic base includes triethylamine, pyridine, N-methylmorpholine, and diisopropylethylamine.

For the reaction, the thioacetic acid salt, thioacetic acid and base are used at 1.0 to 4.0 equivalents, preferably 1.0 to 2.0 equivalents. The solvent includes hydrocarbon halides such as dichloromethane and chloroform; ethers such as tetrahydrofuran and methyl tert-butyl ether; ketones such as acetone and 4-methyl-2-pentanone; acetate esters such as ethyl acetate and isopropyl acetate; nitrites such as acetonitrile; aromatic hydrocarbons such as toluene and xylene; and dimethylformamide and dimethylsulfoxide. The reaction temperature is 0 to 100° C., preferably 20 to 60° C.

The objective compound can be isolated, by removing impurities via procedures such as extraction after completion of the reaction and depositing the crystal in an appropriate solvent. Then, procedures for example column chromatography may also be conducted.

When amino acid side chains are protected, generally, deprotection is conducted finally by a general procedure. Thus, the objective compound can be obtained.

The present invention will now be described in more detail with reference to examples and reference examples, but the invention is not limited to these examples.

REFERENCE EXAMPLE 1

Synthesis of 3-hydroxy-2-methylene-3-phenylpropionate methyl ester

A mixture of benzaldehyde (63.67 g; 600 mmol), methyl acrylate (60 ml; 667 mmol) and 1,4-diazabicyclo [2.2.2] octane (13.46 g; 120 mmol) is stirred at ambient temperature for 119 hours. To the reaction solution is added water (60 ml), 37% hydrochloric acid (60 ml) and ethyl acetate (120 ml), and then, the organic phase is extracted. The resulting organic phase is washed twice with saturated saline (60 ml), dried over anhydrous sodium sulfate and filtered, then concentrated under reduced pressure, to give a crude product of the title compound at a yield of 108.8 g. $^1$H-NMR (CDCl$_3$) d: 3.12 (1H, s), 3.69 (3H, s), 5.55 (1H, s), 5.83 (1H, s), 6.33 (1H, s), 7.29–7.37 (5H, m).

REFERENCE EXAMPLE 2

Synthesis of 2-benzylidene-3-acetoxypropionate methyl ester

The product (108.8 g) in Reference Example 1, namely 3-hydroxy-2-methylene-3-phenylpropionate methyl ester, is dissolved in acetic anhydride (113 ml; 1.20 mol), to which sulfuric acid (0.2 ml) is added, and the resulting mixture is stirred at 100° C. for 4 hours. The reaction solution is concentrated under reduced pressure, to give a crude product of the title compound at a yield of 143.9 g. $^1$H-NMR analysis reveals that the compound is a mixture of the E form and the Z form at a ratio of 87:13.
E form
$^1$H-NMR (CDCl$_3$) d: 2.09 (3H, s), 3.82 (3H, s), 4.95 (2H, s) 7.35–7.45 (5H, m), 7.98 (1H, s).

REFERENCE EXAMPLE 3

Synthesis of 2-benzylidene-3-hydroxypropionic acid

The product (143.9 g) in Reference Example 2, namely 2-benzylidene-3-acetoxypropionate methyl ester, is dissolved in methanol (400 ml), followed by addition of an aqueous solution of sodium hydroxide (96.0 g; 2.40 mol; purity of 97%) in water (800 ml). The resulting mixture is stirred at ambient temperature for 90 minutes. The reaction solution is concentrated under reduced pressure to distill off methanol, followed by addition of water (100 ml) and 36% hydrochloric acid (250 ml) for adjusting the resulting mixture to neutrality and subsequent extraction into ethyl acetate (600 ml). The resulting organic phase is washed with saturated saline (300 ml). After filtering off insoluble matters, the resulting solution is concentrated under reduced pressure. To the resulting residue is added toluene (250 ml×4), and the mixture is concentrated under reduced pressure to remove acetic acid to give a crude product of the title compound (107.8 g).
E form
$^1$H-NMR (CDCl$_3$) d: 4.53 (2H, s), 7.40–7.55 (5H, m), 7.97 (1H, s). MS (ESI); 177.0 ((M—H)—).

REFERENCE EXAMPLE 4

Synthesis of 2-hydroxymethyl-3-phenylpropionic acid

The product (107.8 g) in Reference Example 3, namely 2-benzylidene-3-hydroxypropionic acid, is dissolved in methanol (500 ml), followed by addition of triethylamine (100 ml; 717 mmol) and 5% palladium-carbon (5.00 g; water content of 52.7%) for catalytic reduction in a hydrogen atmosphere for 50 hours. The reaction solution is filtered through Celite to remove the palladium-carbon. The resulting filtrate is subjected to HPLC analysis, indicating that the filtrate contains the title compound (71.0 g; 394 mmol) (at a yield of 65.7% (on a benzaldehyde basis)). The filtrate is concentrated under reduced pressure, and the resulting residue is dissolved in ethyl acetate (600 ml), followed by addition of water (600 ml) and 37% hydrochloric acid (150 ml) and subsequent agitation, to extract the resulting organic phase. The organic phase is washed with an aqueous mixture solution of water (240 ml) and 37% hydrochloric acid and then with saturated saline (300 ml), and dried over anhydrous sodium sulfate. By filtering off the resulting dried matter, the solution is concentrated under reduced pressure, to give a crude product of the title compound. The crude product is dissolved in ethyl acetate (150 ml), followed by addition of hexane (450 ml), and the resulting mixture is gradually cooled from 60° C. to 5° C., to precipitate crystal, which is then filtered and dried to recover the title compound (48.45 g at a purity of 96.5%; 295.5 mmol).
$^1$H-NMR (CDCl$_3$) d: 2.83–2.94 (2H, m), 3.09 (1H, m), 3.70–3.83 (2H, m), 7.20–7.33 (5H, m).

REFERENCE EXAMPLE 5

Synthesis of (S)-2-hydroxymethyl-3-phenylpropionic acid

To (RS)-2-hydroxymethyl-3-phenylpropionic acid (500.0 mg; 2.775 mmol) was added (1R, 2S)-(+)-cis-1-amino-2-indanol (311 mg; 2.085 mmol), followed by addition of 2-propanol (8 ml). While heating the mixture to 70° C. under stirring, the resulting mixture is dissolved therein, followed by gradual cooling. Finally, crystal is precipitated under cooling in an ice bath. The precipitated crystal is filtered under aspiration, washed with a small volume of 2-propanol, and dried under reduced pressure, to give the salt of (S)-2-hydroxymethyl-3-phenylpropionic acid (1R, 2S)-(+)-cis-1-amino-2-indanol (361.1 mg; 79.0% as the yield on the salt basis; optical purity of 95.0% ee). The resulting salt is recrystallized in 2-propanol, to give the salt of (S)-2-hydroxymethyl-3-phenylpropionic acid (1R,2S)-(+)-cis-1-amino-2-indanol at 100% ee (92%). Double decomposition of the resulting salt with hydrochloric acid and extraction into ethyl acetate affords (S)-2-hydroxymethyl-3-phenylpropionic acid (yield of 95%).

Example 1

Synthesis of N-(S-2-hydroxymethyl-1-oxo-3-phenylpropyl) glycine benzyl ester

S-2-Hydroxymethyl-3-phenylpropionic acid (9.00 g; purity of 98.5%; 49.22 mmol) and glycine benzyl ester p-toluene sulfonic acid salt are suspended in tetrahydrofuran (90 ml), followed by addition of triethylamine (7.55 ml; 54.17 mmol) and 2-hydroxybenzotriazole monohydrate (7.32 g; 54.17 mmol), and the resulting mixture is cooled down to 3° C. To the solution is dropwise added a solution of dicyclohexylcarbodiimide (11.17 g; 54.14 mol) in tetrahydrofuran (22 ml) over 15 minutes while the solution is kept at 3 to 4° C., for subsequent reaction at 3 to 4° C. for one hour. After elevating the temperature to ambient temperature, the reaction further progresses for 15 hours. After the precipitated dicyclohexylurea is filtered off, the resulting solution is concentrated under reduced pressure. Then, the resulting residue is dissolved in toluene (100 ml) and ethyl acetate (150 ml), followed by addition of 1 mol/liter hydrochloric acid (200 ml). The resulting mixture is stirred for one hour. After the generated solid is filtered and washed with ethyl acetate (50 ml), the organic phase is separated. The resulting organic phase is sequentially washed with 1 mol/liter hydrochloric acid (60 mol), an aqueous saturated sodium hydrogen carbonate solution (sequentially in 150 ml and 50 ml) and saturate saline (100 ml) and then dried over anhydrous sodium sulfate. After the sodium sulfate is filtered off, the organic phase is concentrated to give a crude product of the title compound. HPLC analysis reveals that the organic phase contains the title compound at 15.86 g (48.44 mmol) (reaction yield of 98.4%; optical purity >99% ee). m.p.: 62° C.
$^1$H-NMR(CDCl$_3$) d:2,65(H, ms), 2.78(1H, dd), 3.01(1H, dd), 3.70–3.80 (2H), 3.87 (1H, dd), 4.17 (1H, dd), 5.14 (1H, d), 5.19 (1H, d), 5.18 (1H, br.t), 7.18–7.41(10H, m). MS (ESI); 328.3 (MH+); [α]D –52.5° © 1.00, MeOH, 25° C.).

Example 2

Synthesis of N-(S-2-methanesulfonyloxymethyl-1-oxo-3-phenylpropyl)-glycine benzyl ester The product in Example 1, namely N-(S-2-hydroxymethyl-1-oxo-3-phenylpropyl)-glycine benzyl ester (15.86 g; 48.44 mmol) is dissolved in toluene (100 ml)and pyridine (15.7 ml; 194.1 mmol), followed by addition of methanesulfonyl chloride (9.37 ml; 121.1 mmol), and the resulting mixture is stirred at ambient temperature for 17 hours. To the reaction solution is added 1 mol/liter hydrochloric acid (150 ml), and the resulting mixture is stirred for 30 minutes. Then, the mixture is subjected to phase separation, and to the resulting organic phase is added an aqueous saturated sodium hydrogen carbonate solution (100 ml). The mixture is then stirred for 30 minutes, followed by phase separation. The resulting organic phase is further washed with saturated saline (100 ml), for HPLC analysis, which indicates that the organic phase contains the title compound at a yield of 19.33 g (47.67 mmol; reaction yield of 98.4%). The organic phase is concentrated, and by subsequently adding toluene (250 ml) to the resulting residue, the residue is dissolved under heating. After filtering off insoluble matters, hexane (100 ml) is added to the resulting solution, followed by heating to 55° C. for dissolving the residue. By gradually cooling the resulting solution to 5° C., the precipitated crystal is obtained by filtration and washed with toluene/hexane (=1/1; 60 ml in total), to give the title compound (17.99 g) (yield after crystal isolation=91.6%)

m.p.: 83 ° C. $^1$H-NMR(CDCl$_3$) d:2.75–2.98 (3H, ms), 3.98 (3H, s), 3.89 (1H, dd), 4.10 (1H, dd), 4.28 (1H, dd), 4.39 (1H, dd), 5.15 (2H, s), 5.97(1H, br. t.), 7.15–7.40 (10H, m). MS (ESI); 306.3 (MH+); [α]D –33.3° © 1.04, MeOH, 25° C.).

Example 3

Synthesis of N-(S-2-bromomethyl-1-oxo-3-phenylpropyl)-glycine benzyl ester

The product in Example 2, namely N-(S-2-methanesulfonyloxymethyl-1-oxo-3-phenylpropyl)-glycine benzyl ester (16.95 g; 42.0 mmol), is dissolved in acetone (120 ml), followed by addition of lithium bromide (7.30 mg; 84.0 mmol) for heating under reflux for 24 hours. After the completion of the reaction, the solvent is distilled off, and ethyl acetate (120 ml) and water (50 ml) are added. The organic layer is separated and then dried over anhydrous magnesium sulfate. After magnesium sulfate is filtered off, the resulting matter is concentrated, to give a crude product of the title compound. HPLC analysis reveals that the title compound is contained in the product at a yield of 16.07 g (41.17 mmol) (reaction yield of 98.0%).

m.p.: 95° C. $^1$H-NMR(CDCl$_3$) d:2.80–3.02 (3H, m), 3.41 (1H, dd:), 3.61 (1H, dd), 3.95 (1H, dd), 4.10 (1H, dd), S.16 (2H, s), 5.92 (1H, br.t), 7.15–7.38 (10H, m). MS (ESI); 390 (MH+); [α]D –33.8° © 1.00, MeOH, 25° C.).

Example 4

Synthesis of N-(S-2-acetylthiomethyl-1-oxo-3-phenylpropyl)-glycine benzyl ester

The product in Example 3, namely N-(S-2-bromomethyl-1-oxo-3-phenylpropyl)-glycine benzyl ester (834.5 mg; 2.14 mmol), is dissolved in methyl isobutyl ether (4 ml), followed by addition of potassium thioacetate (256 8 mg; 2.57 mmol) and stirring at 50° C. for 3.5 hours. After the completion of the reaction, the organic phase is extracted into ethyl acetate (30 ml) and water (5 ml), and is then washed with an aqueous saturated sodium hydrogen carbonate solution (5 ml) and saturated saline (5 ml), followed by addition of active charcoal (2 mg) and stirring at ambient temperature for 20 minutes. The resulting matter is dried over anhydrous magnesium sulfate. After the active charcoal and magnesium sulfate are filtered off, the resulting matter is concentrated, to give a crude product of the title compound (842.3 mg). By adding methyl t-butyl ether (4.2 ml) to the resulting crude product and cooling the mixture from ambient temperature to 0° C. under stirring, crystal is precipitated. The precipitated crystal is filtered and washed with methyl t-butyl ether (1 ml), to give the title compound (416.4 mg; yield of 50% after crystal isolation; optical purity >99% ee).

m.p.: 59–60°° C. $^1$H-NMR (CDCl$_3$) d:2.31 (3H, s), 2.62–2.67 (3H, m), 2.62–2.67 (3H, m), 2.87–3.07 (2H, dd), 3.08–3.11 (1H, dd), 3.85 (1H, dd), 4.07 (1H, dd), 5.13 (2H, s), 5.83 (1H, br.t.), 7.14–7.39 (10H,m). MS (ESI); 386.2 (MH+); [α]D +23.0° © 1.00, MeOH, 25° C.).

Example 5

Synthesis of N-(S-2-acetylthiomethyl-1-oxo-3-phenylpropyl)-glycine benzyl ester

Potassium thioacetate (386 mg; 3.31 mol) is suspended in methyl isobutyl ether (6 ml) followed by dropwise addition of a solution of N-(S-2-methanesulfonyloxymethyl-1-oxo-3-phenylpropyl)-glycine benzyl ester (812.9 mg; 2.01 mmol) in methyl isobutyl ether (11 ml), and the resulting mixture is stirred at ambient temperature for 3 hours. After the completion of the reaction, an aqueous saturated sodium hydrogen carbonate solution (20 ml) is added to the resulting matter, and then the organic phase is extracted, washed with saturated saline (20 ml) and dried over magnesium sulfate. After filtering off magnesium sulfate, the resulting matter is concentrated. Subsequently, the resulting residue is purified by silica gel chromatography, to recover the title compound of 742.7 mg (at a yield of 97%).

Example 6

Synthesis of N-(S-2-(p-toluenesulfonyl)methyl-1-oxo-3-phenylpropyl)-glycine benzyl ester 327.4 mg of N-(S-2-hydroxymethyl-1-oxo-3-phenylpropyl)-glycine benzyl ester (1.0 mmol), is dissolved in dichloromethane (5 ml), followed by addition of pyridine (0.18 ml; 2.2 mmol) and p-toluenesulfonyl chloride (381.3 mg; 2.0 mmol) for stirring at ambient temperature for 4 days. The solvent is distilled off, and the resulting matter is subjected to silica gel chromatography with an ethyl acetate-hexane solution, to give the title compound at a yield of 373.1 mg (0.77 mmol) (yield of 77.5%).

$^1$H-NMR(CDCl$_3$) d:2.42 (3H, s), 2.73–2.87 (3H, m), 3.90–3.94 (2H, m), 4.05–4.21(2H, m), 5.14 (2H, s), 6.05 (1H, br.t.), 7.15–7.74 (14H, m). MS (ESI); 481.5 (MH+);

Example 7

Synthesis of N-(S-2-(p-nitrobenzenesulfonyl)methyl-1-oxo-3-phenylpropyl)-glycine benzyl ester 327.4 mg of N-(S-2-hydroxymethyl-1-oxo-3-phenylpropyl)-glycine benzyl ester (1.0 mmol), is dissolved in dichloromethane (5 ml), followed by addition of pyridine (0.24 ml; 3.0 mmol) and p-toluenesulfonyl chloride (738.8 mg; 3.0 mmol) for stirring at ambient temperature for 20 hours. The solvent is distilled off, and the resulting matter is purified by silica gel chromatography with an ethyl acetate-hexane solution, to give the title compound of 331.6 mg (0.65 mmol) (yield of 65.0%).

$^1$H-NMR(CDCl$_3$) d:2.73–2.88 (3H, m), 3.84 (1H, dd), 4.03-(1H, dd) 4.20 (1H, dd) 4.31 (1H, dd), 5.15 (2H, s), 5.92 (1H, br. t.), 7.08–7.40 (10H, m), 8.02–8.06 (10H, m), 8.31–8.35 (10H, m). MS (ESI); 513.1 (MH+);

Example 8

Synthesis of N-(S-2-acetylthiomethyl-1-oxo-3-phenylpropyl)-glycine benzyl ester 157.3 mg of N-(S-2-(p-nitrobenzene sulfonyl)methyl-1-oxo-3-phenylpropyl)-glycine benzyl ester (0.31 mmol), is dissolved in methyl isobutyl ether (1 ml), followed by addition of potassium thiolacetate (70.0 mg; 0.61 mmol) for stirring at ambient temperature for 5 hours. After the completion of the reaction, ethyl acetate (20 ml) and an aqueous saturated sodium hydrogen carbonate solution (5 ml) are added to the reaction solution. The organic layer is separated, and is then dried over magnesium sulfate. After filtering off magnesium sulfate, the resulting matter is concentrated, to give the title compound (104.1 mg; 0.27 mmol; yield of 88.0%).

As has been described above, in accordance with the present invention, optically active N-(S-2-acetylthiomethyl-1-oxo-3-phenylpropyl)-glycine benzyl ester can be produced at low cost in an industrial manner.

The disclosure of the priority document, Application No. 32791/1998, which was filed in Japan on Feb. 16, 1998, is incorporated by reference herein in its entirety.

Having thus described the invention in detail, it will be understood that these details need not be strictly adhered to, but that various changes or modifications may suggest themselves to those skilled in the art, all falling within the scope of the invention as defined by the claims.

What is claimed is:

1. A method of producing an optically active N-(2-acetylthilmetyl-10oxo-3-phenylpropyl)-amino acid ester, represented by the general formula (IV):

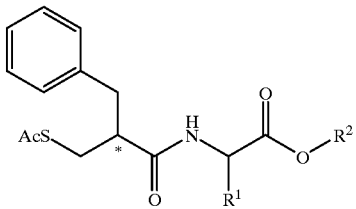

(IV)

wherein $R^1$ represents hydrogen, an amino acid side chain or a protected amino acid side chain;

$R^2$ represents a linear or branched $C_1$ to $C_{18}$ alkyl group, or a benzyl group which may or may not have a substitutent;

AcS represents an acetylthio group; and

\* represents an optically active carbon atom, comprising:

reacting an optically active N-acylamino acid ester represented by the formula (III):

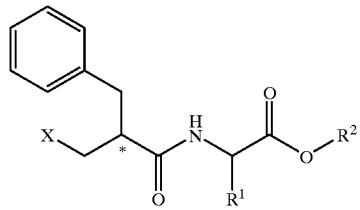

(III)

wherein $R^1$ and $R^2$ independently represent the same as described above;

X represents chlorine, bromine, iodine, a linear, branched or cyclic $C_1$–$C_6$ alkylsulfonyloxy group which may or may not have a substituent, or a $C_6$–$C_{18}$ arylsulfonyloxy group; and \* represents the optically active carbon atom, with a thioacetate salt or thioacetic acid in the presence of a base.

2. The method according to claim 1, wherein the optically active carbon atom is in the configuration S.

3. The method according to claim 1, wherein the optically active carbon atom is in the configuration R.

4. The method according to claim 1, wherein $R_1$ represents hydrogen and $R_2$ represents a benzyl group.

5. The method according to claim 4, wherein the optically active carbon atom is in the configuration S.

6. The method according to claim 4, wherein the optically active carbon atom is in the configuration R.

* * * * *

UNITED STATES PATENT AND TRADEMARK OFFICE
CERTIFICATE OF CORRECTION

PATENT NO. : 6,239,305 B1
DATED : May 29, 2001
INVENTOR(S) : Takayuki Suzuki et al.

It is certified that error appears in the above-identified patent and that said Letters Patent is hereby corrected as shown below:

Column 1,
Line 24, "deteriorated cardiovascular system, hypertension, cardiac" should read -- cardiovascular system deterioration, hypertension, cardiac --.

Column 4,
Line 34, "acid (1) for" should read -- acid (I) for --;
Line 37, "such as (IR,2S)-(+)-cis-1-amino-2-" should read -- such as (1R,2S)-(+)-cis-1-amino-2- --;
Line 59, "a-carboxyl group" should read -- α-carboxyl group --.

Column 5,
Line 6, "acid (1) with" should read -- acid (I) with --;
Line 41, "action of an sulfonation" should read -- action of a sulfonation --;
Line 63, "acid (1) can be converted into-optically" should read -- acid (I) can be converted into optically --.

Column 8,
Line 52, "d:2,65(H,ms)," should read -- d:2.65(H,ms), --;
Line 53, "3.70-3.80 (2H)," should read -- 3.70-3.80 (2H, m), --.

Column 9,
Line 56, "(256 8 mg; 2.57 mmol)" should read -- (256.8 mg; 2.57 mmol) --.

Column 10,
Line 7, "m.p.: 59-60°° C." should read -- m.p.: 56-60°C. --.

UNITED STATES PATENT AND TRADEMARK OFFICE
CERTIFICATE OF CORRECTION

PATENT NO.   : 6,239,305 B1
DATED        : May 29, 2001
INVENTOR(S)  : Takayuki Suzuki et al.

It is certified that error appears in the above-identified patent and that said Letters Patent is hereby corrected as shown below:

Column 11,
Line 24, "acetylthilmetyl-10oxo-3-phenylpropyl)-amino" should read
-- acetylthiomethyl-1-oxo-3-phenylpropyl)-amino --;
Line 42, "substitutent;" should read -- substituent; --.

Signed and Sealed this

Eighteenth Day of December, 2001

*Attest:*

*Attesting Officer*

JAMES E. ROGAN
*Director of the United States Patent and Trademark Office*